United States Patent [19]
Hofmann

[11] Patent Number: 4,787,388
[45] Date of Patent: Nov. 29, 1988

[54] METHOD FOR OPENING CONSTRICTED REGIONS IN THE CARDIOVASCULAR SYSTEM

[75] Inventor: Eugen Hofmann, Zurich, Switzerland

[73] Assignee: Schneider - Shiley AG, Zurich, Switzerland

[21] Appl. No.: 935,467

[22] Filed: Nov. 26, 1986

Related U.S. Application Data

[63] Continuation-in-part of Ser. No. 842,562, Mar. 21, 1986, abandoned.

[30] Foreign Application Priority Data

Nov. 29, 1985 [CH] Switzerland .................. 5108/85

[51] Int. Cl.$^4$ ............................................. A61M 29/02
[52] U.S. Cl. ................................ 128/344; 128/348.1
[58] Field of Search ..................... 128/344, 348.1, 343, 128/325; 604/101, 96

[56] References Cited

U.S. PATENT DOCUMENTS

| | | | |
|---|---|---|---|
| 3,504,662 | 4/1970 | Jones | 128/344 X |
| 4,040,413 | 8/1977 | Ohshiro | 604/101 X |
| 4,183,102 | 1/1980 | Guiset | 604/101 X |
| 4,195,637 | 4/1980 | Gruntzig et al. | 128/348 |
| 4,327,736 | 5/1982 | Inoue | 128/349 B |
| 4,418,688 | 12/1983 | Loeb | 128/6 |
| 4,484,579 | 11/1984 | Meno et al. | 128/305 |
| 4,546,759 | 10/1985 | Solar | 604/101 X |

FOREIGN PATENT DOCUMENTS 8301893  6/1983  World Int. Prop. O. .

OTHER PUBLICATIONS

Erbel, et al., "New Balloon Catheter for Prolonged Percutaneous Transluminal Coronary Angioplasty and Bypass Flow in Occluded Vessels", Catheterization and Cardiovascular Diagnosis, vol. 12, pp. 116–123 (1986).
Cribier, A. et al., "Percutaneous Transluminal Valvuloplasty of Acquired Aortic Stenosis in Elderly Patients: An Alternative to Valve Replacement?", The Lancet, pp. 63–67 (Jan. 11, 1986).

Primary Examiner—Michael H. Thaler
Attorney, Agent, or Firm—Charles J. Knuth; Peter C. Richardson; Lawrence C. Akers

[57] ABSTRACT

A catheter for opening constricted regions in the cardiovascular system includes an expandable dilatation zone comprising three dilatation elements arranged around a support tube. The dilatation elements are of tubular configuration, and each communicates at one end with a passage in the support tube leading to a pressure-suction pump. Constricted regions in the cardiovascular system may be enlarged or opened by introducing the dilatation zone into the affected site in a folded condition and expanding it peripherally therein. Upon expansion of the dilatation elements flow passages are formed between these elements, through which body fluid (for example blood) can pass with little resistance. The supply of body fluid to organs and tissues downstream of the affected site is thereby maintained. Interruption of the dilatation treatment is not required to insure this supply, thus permitting a substantial reduction in the overall duration of the medical procedure. The catheter may be employed, for example, to dilate blood vessels constricted by arteriosclerotic lesions and in valvuloplasty procedures, and may also be employed for treating constrictions in the esophagus.

6 Claims, 1 Drawing Sheet

METHOD FOR OPENING CONSTRICTED REGIONS IN THE CARDIOVASCULAR SYSTEM

This is a continuation-in-part of my U.S. patent application Ser. No. 842,562, filed Mar. 21, 1986 now abandoned.

BACKGROUND OF THE INVENTION

The present invention relates to a catheter for opening constricted regions in the cardiovascular system of a patient.

Catheters of this kind have been in use for some time, for example to treat arteriosclerotic vascular constrictions. Such catheters have an expandable balloon at the distal end, to be brought into the region of constriction in a folded condition. By means of a passage accessible from the outside of the catheter, the balloon is filled with fluid so that it expands peripherally, and the tissue bringing about the constriction is pressed outward into the vessel wall.

The expanded balloon blocks the vessel completely, so that the treatment must be periodically interrupted after brief intervals, for example to prevent distal ischemia. Owing to the necessary interruptions, the over-all duration of treatment is correspondingly lengthened.

It is an object of the present invention to provide a catheter of the aforementioned kind whereby, even during a prolonged dilatation of the constriction, the continuous supply of blood and oxygen to the downstream organs and tissues is maintained, which catheter is economical in manufacture and yet dependable in operation.

SUMMARY OF THE INVENTION

This and other objects of the invention are achieved with a novel catheter including an expandable dilatation zone comprising a plurality of dilatation elements arranged around an elongated support tube, with each of the dilatation elements being of elongated tubular configuration and extending in the lengthwise direction of the support tube.

In the expanded condition, the dilatation elements and the wall of the treated vessel form several passages through which body fluid or a gas can freely pass. Thus, in the case of three dilatation elements arranged side-by-side around the support tube, three of such passages are formed peripherally between the wall of the treated vessel and the walls of adjacent dilatation elements, each of these passages extending through the dilatation zone in the lengthwise direction of the catheter. Passage of the body fluid through the dilatation zone is assured even if some of the passages are blocked.

Since, instead of one large dilatation element, a plurality of correspondingly smaller dilatation elements are employed, a higher dilatation pressure is obtainable. This is because smaller dilatation elements can be subjected to a higher internal pressure. Thus, for example, a tubular dilatation element about 18 mm in diameter may be subjected to an internal pressure of only about 200,000 Pa, whereas a similar dilatation element about 8 mm in diameter will withstand an internal pressure of about 800,000 Pa.

Compared to the known catheters of this kind, the overall duration of treatment can be shortened substantially, because dilatation of the constriction need not be interrupted periodically to insure an adequate supply of body fluid to tissues and organs.

The present invention also comprises a novel method of opening a constricted region in the cardiovascular system of a patient comprising the use of a novel catheter of the invention.

Further advantageous features and refinements of the invention are described elsewhere in the present application.

DETAILED DESCRIPTION OF THE INVENTION

An embodiment of the invention will be described in more detail, by way of example only, with reference to the drawings. In the drawings:

FIG. 4 shows a longitudinal section of the dilatation zone of the catheter of FIG. 1.

Figure 1:
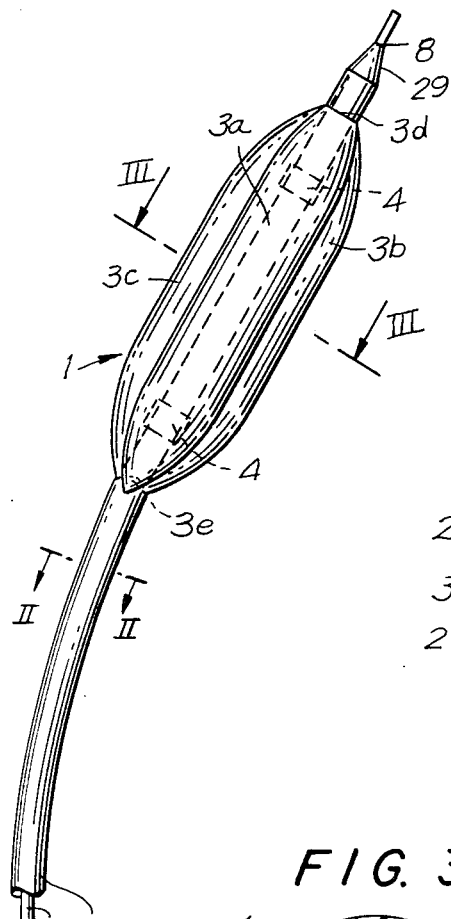
FIG. 1 shows a catheter of the invention having three dilatation elements to a greatly enlarged scale.
Figure 8:
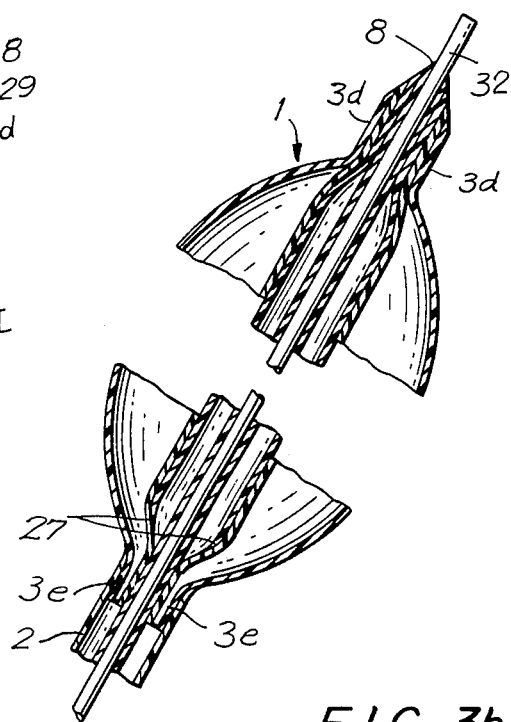
Figure 2A:
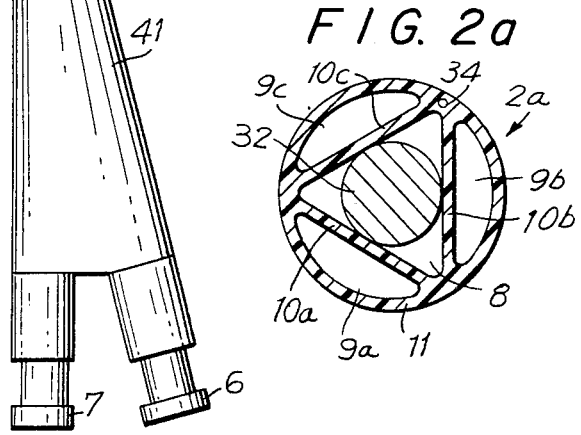
FIGS. 2a and 2b show cross-sections of alternative support tubes taken at the line II—II in FIG. 1.
Figure 2B:
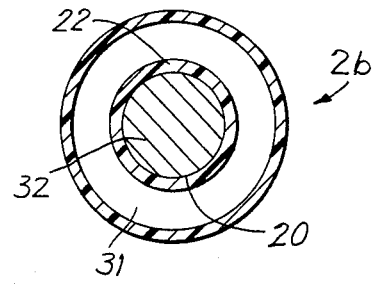

In the catheter represented in FIG. 1, the dilatation zone 1 of the catheter comprises three dilatation elements 3a–c, in bundled side-by-side arrangement around a support tube 2. The dilatation elements 3a–c are each closed at one end 3d and open at the other end 3e. The ends 3d are fixed, for example welded, to the outside of the support tube 2. The open ends 3e are each inserted into an opening 27 of the support tube 2 and fixed therein and to the inside of the support tube 2 (FIG. 4), for example bonded with a cyanoacrylate adhesive. Examples of the support tube 2 are shown in FIGS. 2a and 2b and described further below. The interiors of the dilatation elements 3a–c communicate by way of passages 9a–c (FIG. 2a) or by way of a common annular passage 31 (FIG. 2b) with a pressure-suction pump, known per se and not shown in the figures. Between the ends 3d and 3e of the dilatation elements 3a–c, the support tube 2 may be single-lumened, or of the same configuration as outside this zone.

The dilatation elements 3a–c each inherently exhibit cross-sectionally in the expanded condition a substantially circular wall, but may alternatively be of a different cross-sectional shape instead, e.g. elliptical, depending on the specific application. The inflation of the dilatation elements 3a–c may be effected in known manner with a liquid medium or gas. For this purpose, the interiors of the dilatation elements 3a–c are preferably interconnected, so that they may be respectively expanded simultaneously. When using the support tube of FIG. 2a, the passages 9a–c are joined on the pump side for this purpose. Conceivably, however, the dilatation elements 3a–c may instead be separately supplied and independently inflated.

The support tube 2 has a passage 8 or 20 leading to the outside at the tip 29, through which a guide wire 32 may be thrust, or contrast media as well as medication delivered. On the support tube 2, marking elements 4 of a suitable metal may be provided for locating the dilatation zone by X-rays.

The support tube 2 is connected to a fitting 1 provided with a connection 6 for the pressure-suction pump, and a gauge and injection connection 7.

The use of a support tube 2a as in FIG. 2a has been found especially suitable. It has a cylindrical wall 11 subdivided internally by partitions 10a–c into a triangular inner passage 8 and three outer passages 9a–c. The outer passages 9a–c lead to the pressure--suction pump and to the dilatation elements 3a–c, while the inner passage 8 opens to the outside at the tip 29. An additional lumen 34 opening to the outside on the proximal side (i.e. the lower side in FIG. 1) of the dilatation zone 1 may be provided in the cylindrical wall 11 at the junction of two partitions (e.g. partitions 10b and 10c). The provision of lumens 8 and 34 enables measurement of the blood pressure drop across an affected region in the cardiovascular system so that the progress of a constriction-opening medical procedure can be more carefully monitored. However, the configuration of the support tube may instead be as shown in FIG. 2b. This double-lumened tube 2b has an outer annular passage 31 communicating with the dilatation elements 3a–c. A coaxial inner wall 22 forms an inner passage 20 through which a guide wire 32 may be thrust. In this embodiment the spaces in passage 31 between the respective ends 3e of the dilatation elements are filled with pieces of a suitable sealing material such as an epoxy polymer (not shown in the figures). The tubes 2a and 2b are flexible and may be made of a suitable plastic, for example by extrusion.

Figure 3A:
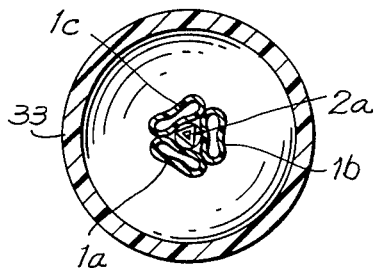
FIG. 3a shows a cross-section of an unexpanded dilatation zone with folded walls taken at the line III—III in FIG. 1 and, schematically, the wall of a constricted body vessel.
Figure 3B:
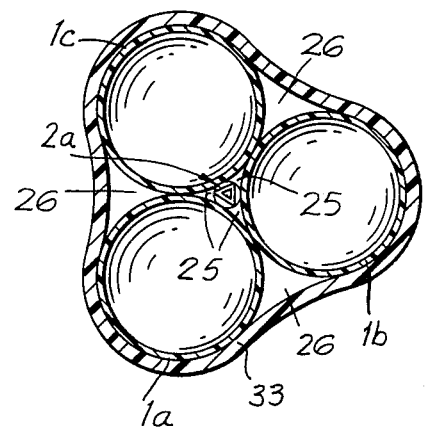
FIG. 3b is identical to FIG. 3a, except that the dilatation elements are expanded peripherally.

The catheter according to the invention is brought into the region of the place to be dilated with the aid of the guide wire 32 in a manner known per se, with the dilatation elements 3a–c folded as schematically represented in FIG. 3a. The dilatation elements 3a–c are then expanded to the required size by increased pressure. In this condition, the walls 1a–c of the dilatation elements 3a–c shown in the figures are substantially circular in cross-section and press externally against the wall 33 of the constriction (FIG. 3b). Upon inflation of the dilatation elements 3a–c, central passages 25 and peripheral passages 26 are formed, extending through the dilatation zone 1 in the lengthwise direction of the catheter, so that body fluid can pass through zone 1 with only slight resistance.

Since the flow of the body fluid is not interrupted, a period of therapeutic intervention of adequate length, during which the dilatation of the constriction need not be interrupted, is available. Compared to the use of known catheters, the overall duration of the treatment can thereby be reduced substantially.

The catheter according to the invention may be used to enlarge constrictions in all sorts of vessels carrying body fluids. Examples of other fields of application are the treatment of constrictions in the esophagus or in the bile duct. Simultaneously with the dilation of the constriction, chemical substances may be introduced into the body through the central passage, or, for example, the blood pressure may be measured.

The catheter of the invention is particularly suitable for use in valvuloplasty procedures, in which the leaflets of stenotic heart valves, in particular the aortic and mitral valves, are forced apart to re-open the valve and restore it to full function, without having to perform open heart surgery. The advantages of the use of the catheter of the present invention (as compared to a dilatation catheter having only a single expandable dilatation element) are the provision for blood flow through the expanded dilatation zone (as described above), the increased surface pressure that can be applied to force open the valve and, when three dilatation elements are employed as shown in the figures herein, the capability to concentrate that pressure at 120° intervals (as viewed in FIG. 3b), which is ideally suited for opening the calcified seams of stenotic tri-leaflet valves.

In a preferred valvuloplasty procedure for opening a stenotic aortic valve, for example, a catheter of the invention (with the dilatation elements folded and non-expanded) carrying an appropriate guide wire 32 may be inserted through a suitable guiding catheter into the femoral artery. The catheter and guide wire are advanced together to the end of the guiding catheter, after which the guide wire is advanced by itself to the stenotic valve and through the remaining opening thereof. The catheter of the invention is then advanced along the guide wire until the dilatation zone is positioned in the valve opening, and the dilatation elements are then expanded to open the valve. After deflating the dilatation elements the catheter of the invention, guide wire and guiding catheter are withdrawn from the patient's body.

I claim:

1. A method for opening a constricted region in the cardiovascular system of a patient comprising the steps of:
   (a) providing a catheter comprising an elongated support tube having distal and proximal ends, a radially expandable dilatation means carried by and integrally connected to said support tube adjacent the distal end thereof, and means for expanding and contracting said dilation means, with said dilatation means comprising a plurality of dilatation elements arranged circumferentially around the support tube and each presenting a smoothly-rounded exterior surface free of sharp edges;
   (b) inserting the distal end of said catheter into the cardiovascular system of the patient with said dilatation means in an unexpanded condition;
   (c) advancing said catheter within said cardiovascular system until said dilatation means is situated within said constricted region;
   (d) expanding the dilatation means to open the constricted region while permitting the patient's blood to flow through the expanded dilatation means, between the dilatation elements and outside the support tube;
   (e) contracting the dilatation means; and
   (f) withdrawing said catheter from the body of the patient.

2. A method of claim 1 wherein each of said dilatation elements are of elongated configuration and extend in the lengthwise direction of the support tube.

3. A method of claim 2 wherein said plurality of dilatation elements are substantially uniformly arranged circumferentially around the support tube.

4. A method of claim 3 wherein said catheter includes means placing the interiors of all of said dilatation elements in fluid communication with one another so that said elements can only be simultaneously expanded and contracted and are not capable of being independently expanded or contracted.

5. A method of claim 2 wherein said dilatation elements are tubular and are each attached at their respective ends to the support tube.

6. A method of claim 2 wherein each of said dilatation elements has a substantially circular shape in transverse cross section when expanded and unrestrained.

* * * * *

UNITED STATES PATENT AND TRADEMARK OFFICE
CERTIFICATE OF CORRECTION

PATENT NO. : 4,787,388

DATED : November 29, 1988

INVENTOR(S) : Eugen Hofmann

It is certified that error appears in the above-identified patent and that said Letters Patent is hereby corrected as shown below:

In line 66 of column 2, change "fitting 1" to --fitting 41--.

In line 9 of claim 1, at line 30 of column 4, change "dilation" to --dilatation--.

Signed and Sealed this

Twenty-eighth Day of March, 1989

Attest:

DONALD J. QUIGG

Attesting Officer

Commissioner of Patents and Trademarks